(12) United States Patent
Ichikawa et al.

(10) Patent No.: US 9,155,667 B2
(45) Date of Patent: Oct. 13, 2015

(54) PANTS-TYPE WEARING ARTICLE

(75) Inventors: Makoto Ichikawa, Kagawa (JP);
Kenichi Sasayama, Kagawa (JP);
Kunihiko Katsuragawa, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 511 days.

(21) Appl. No.: 13/580,198

(22) PCT Filed: Mar. 4, 2011

(86) PCT No.: PCT/JP2011/001300
§ 371 (c)(1),
(2), (4) Date: Aug. 21, 2012

(87) PCT Pub. No.: WO2011/108286
PCT Pub. Date: Sep. 9, 2011

(65) Prior Publication Data
US 2012/0311771 A1 Dec. 13, 2012

(30) Foreign Application Priority Data
Mar. 5, 2010 (JP) .................. 2010-049745

(51) Int. Cl.
*A61F 13/15* (2006.01)
*A61F 13/49* (2006.01)
(Continued)

(52) U.S. Cl.
CPC ....... *A61F 13/49011* (2013.01); *A61F 13/4902* (2013.01); *A61F 13/496* (2013.01); *A61F 13/49017* (2013.01); *A61F 13/49413* (2013.01); *A61F 13/4906* (2013.01); *A61F 13/70* (2013.01)

(58) Field of Classification Search
CPC ............ A61F 13/496; A61F 13/79058; A61F 13/4906; A61F 13/49061; A61F 13/49063; A61F 13/505; A61F 13/49011; A61F 13/49012; A61F 13/49406; A61F 13/49413; A61F 13/565; A61F 13/5655; A61F 13/64; A61F 13/66; A61F 3/68; A61F 13/70; A61F 13/72; A61F 13/76; A61F 13/78; A61F 13/80; A61F 13/5515
See application file for complete search history.

(56) References Cited

U.S. PATENT DOCUMENTS 4,743,246 A * 5/1988 Lawson ................... 604/385.27
2005/0004545 A1 1/2005 Shimada et al.
(Continued)

FOREIGN PATENT DOCUMENTS

EP 1552801 A1 7/2005
JP 2004329657 A 11/2004
(Continued)

OTHER PUBLICATIONS http://www.merriam-webster.com/dictionary/gather, Jan. 17, 2015.*
(Continued)

*Primary Examiner* — Lynne Anderson
*Assistant Examiner* — Bradley Philips
(74) *Attorney, Agent, or Firm* — Hauptman & Ham, LLP

(57) ABSTRACT

A pant-type wearing article comprises a front panel, a rear panel and a central panel. The front panel cooperates with the rear panel to form a waist region. The central panel includes a front end portion separably joined to the outer side of the waist region and a rear end portion separably joined to the outer side of the waist region. Side edges of the front end portion opposed to each other in the transverse direction are formed with front side corner regions and side edges of the rear end portion opposed to each other in the transverse direction are formed with rear side corner regions. At least one of the paired front side corner regions and the paired rear side corner regions is not joined to the outer surface of the waist region to form a gripper region.

13 Claims, 6 Drawing Sheets

(51) Int. Cl.
   *A61F 13/494* (2006.01)
   *A61F 13/496* (2006.01)
   *A61F 13/70* (2006.01)

(56) References Cited

U.S. PATENT DOCUMENTS

2005/0107764 A1    5/2005   Matsuda et al.
2005/0177124 A1    8/2005   Kondo et al.
2007/0282292 A1*  12/2007   Harkness ..................... 604/396
2009/0275909 A1*  11/2009   Sakaguchi ............... 604/385.23

FOREIGN PATENT DOCUMENTS

JP    2006051240 A    2/2006
JP    2007522912 A    8/2007
JP    2008104503 A    5/2008

OTHER PUBLICATIONS

Extended European Search Report dated Nov. 18, 2013, corresponds to European patent application No. 11750399.5.
International Search Report and Written Opinion for PCT/JP2011/001300, dated May 10, 2011.

* cited by examiner

PANTS-TYPE WEARING ARTICLE

RELATED APPLICATIONS

The present application is National Phase of International Application Number PCT/JP2011/001300, filed Mar. 4, 2011, and claims priority from Japanese Application Number 2010-049745, filed Mar. 5, 2010.

TECHNICAL FIELD

The present invention relates to pant-type wearing articles and more particularly to pant-type wearing articles having component panels which form the pant-type wearing articles capable of easily separating one from another.

RELATED ART

In conventional pant-type wearing articles, same of them comprise the component members adapted to be separated after use of the articles. For example, the disposable diaper disclosed in JP 2006-51240 A (PATENT DOCUMENT 1) is of pant-type and comprises an annular waist member and a flat pad-like crotch member. The crotch member is bowed in a U-shape and detachably attached to the waist member by fastener means such as planar fasteners.

CITATION LIST

Patent Literature

[PATENT DOCUMENT 1] JP 2006-51240 A

SUMMARY OF INVENTION

Problem to be Solved by the Invention

When some component members of pant-type diapers can be easily separated one from another, disposal of the diapers after used can be advantageously simplified. In view of such advantages, one or more of embodiments of the present invention aims to provide the pant-type wearing articles improved so that the component members can be easily separated without any detachably attachment means.

Measure to Solve the Problem

One or more aspects of the present invention is characterized in features as will be described below: a pant-type wearing article having a transverse direction and a vertical direction, comprising a front panel, a rear panel and a central panel, side edges of the front panel opposed in the transverse direction being joined to side edges of the rear panel opposed in the transverse direction to form an annular waist region, the central panel being folded in the vertical direction to define two upper end portions, and one of the two upper end portions being joined to the outside of the front panel and the other of the two upper end portions being joined to the outside of the rear panel.

In this article, at least one of the front panel and the rear panel is provided with a plurality of elastic members extending in the transverse direction under tension and adapted to be formed with gathers forming crests and troughs repeating in the transverse direction upon contraction of the elastic members; the central panel has the one of the two upper end portions separably joined to the front panel and the other of the two upper end portions separably joined to the rear panel; and the two upper end portions respectively have ends extending in the transverse direction and both side edges extending in the vertical direction wherein the both side edges intersect with the ends to form a pair of corner regions in each of the ends and at least one of the corner regions overlaps the gathers and not joined to the outer surface of the waist region to define a gripper region adapted to be held by the user's or caretaker's fingers.

DETAILED DESCRIPTION OF THE PREFERRED EMBODIMENTS

Details of the present invention will be more fully understood from the description of the pant-type diaper a as a typical embodiment of the pant-type wearing article made hereunder with reference to the accompanying drawings.

Figure 1:
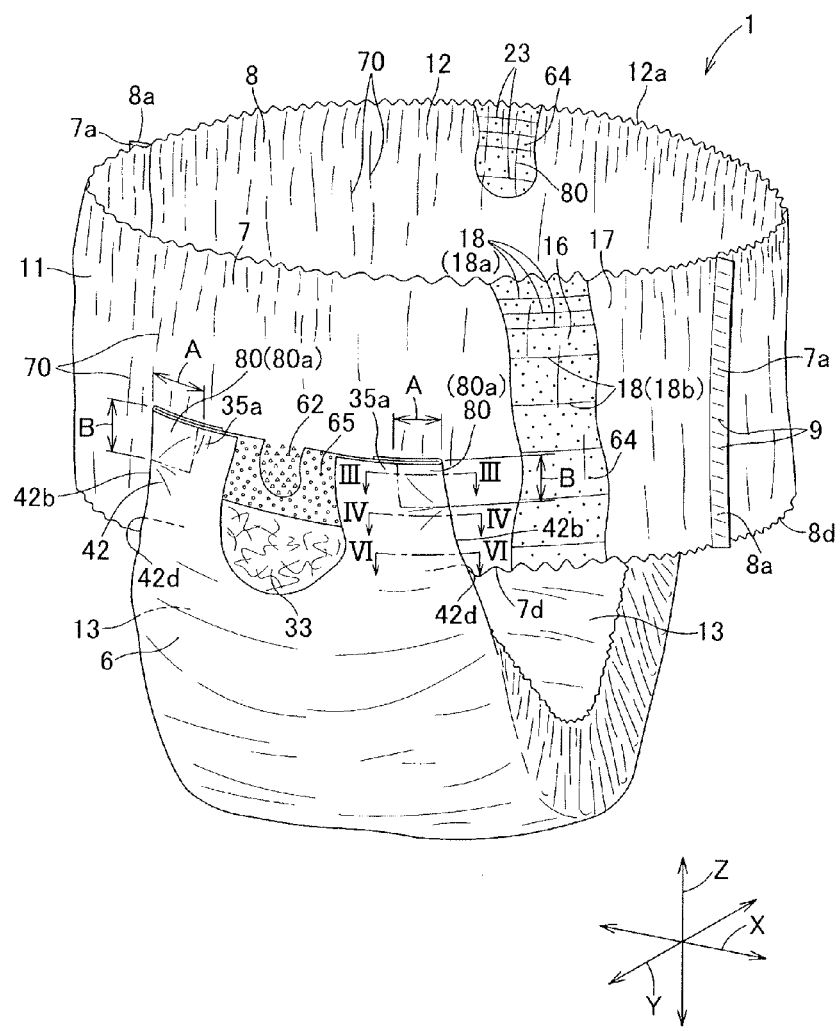
FIG. 1 is a partially cutaway perspective view of a pant-type diaper as one embodiment of the present invention.

Referring to FIG. 1, a diaper 1 at least comprises a front panel 7, a rear panel 8 and a central panel 6. The diaper 1 has a transverse direction X, a front-back direction Y and a vertical direction Z wherein side edges 7a, 7a of the front panel 7 opposite in the transverse direction X and side edges 8a, 8a of the rear panel 8 opposite in the transverse direction X are put flat and joined together at seam-welded regions 9 to form an annular waist region 11 and a waist-opening 12. The central panel 6 is folded in two in the vertical direction Y, and the central panel 6 is joined at a front end 42 thereof to the outside of the front panel 7 with hot melt adhesives 62 as well as at a rear end 43 thereof to the outside of the rear panel 8 with hot melt adhesives 63 (See FIG. 2) to hang down from the waist region 11. The front and rear panels 7, 8 and the central panel 6 joined together in this manner define a pair of leg-openings 13. Referring to FIG. 1, the front panel 7 comprises an inner sheet 16 facing the wearer's skin (not shown), an outer sheet 17 facing the wearer's garment and front waist elastic members 18 sandwiched between these inner and outer sheets 16, 17. The inner and outer sheets 16, 17 are joined to each other with hot melt adhesives 64 (See FIG. 2) and the front waist elastic members 18 are joined under tension to at least one of the inner and outer sheets 16, 17 with hot melt adhesives (not shown). In FIG. 1, the front waist elastic members 18 are left contract circumferentially of the waist region 11 and thereby the outer sheet 17 is formed with gathers defined by crests 71 and troughs 72 (See FIG. 3) repeating circumferentially thereof.

Figure 2:
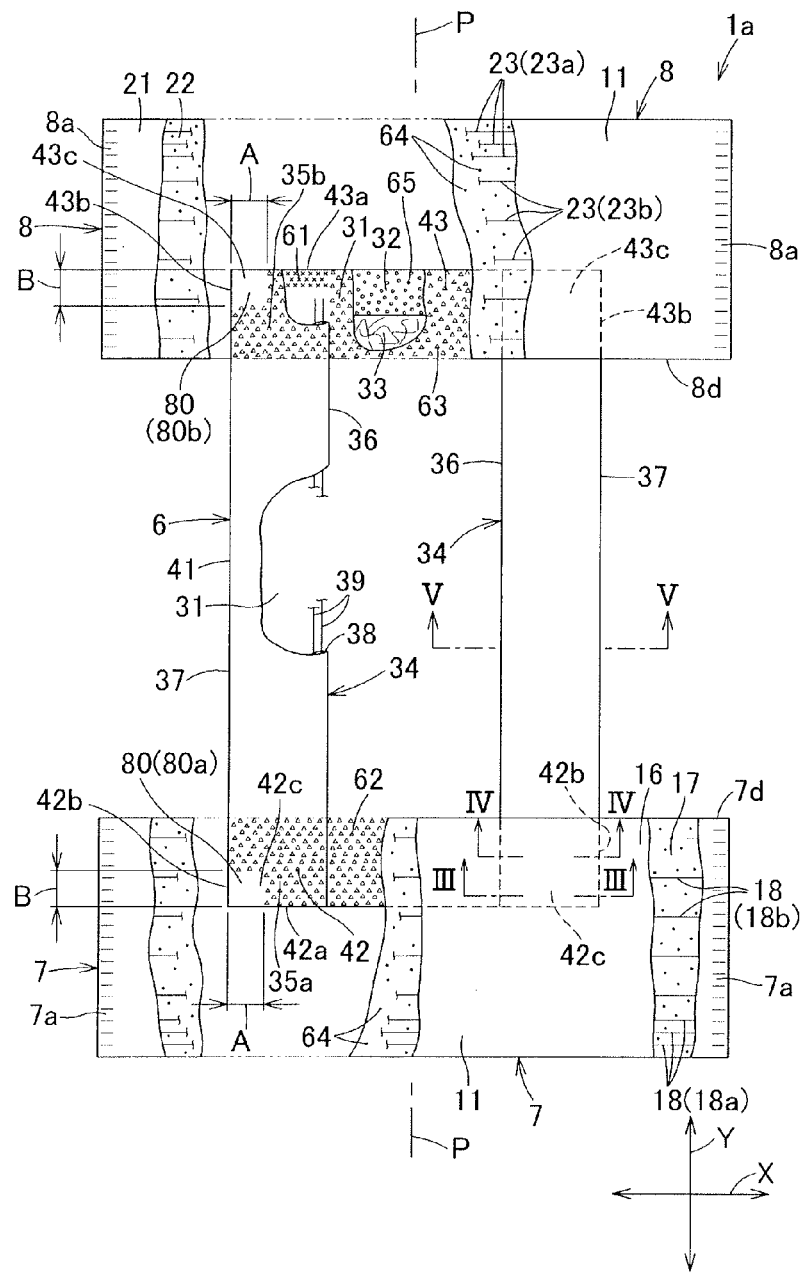
FIG. 2 is a partially cutaway plan view of the pant-type diaper of FIG. 1 in its flatly developed state.

Referring to FIG. 2, front and rear panels 7, 8 extend generally in the vertical direction Z together with the central panel 6 in FIG. 1 now extend generally in the front-back direction Y. These front panel 7, rear panel 8 and central panel 6 are shaped symmetrically about a center line P bisecting a dimension of the developed diaper 1*a* in the transverse direction X.

The front waist elastic members 18 in the front panel 7 shown in FIG. 2 specifically comprise, as will be seen in FIG. 1, a plurality of upper elastic members 18*a* closely spaced one from another and circumferentially extending along a peripheral edge 12*a* of the waist-opening 12 and a plurality of lower elastic members 18*b* widely spaced one from another and more widely than the upper elastic members 18*a* in the vertical direction Z. While the front waist elastic members 18 are kept stretched in the transverse direction X and the inner and outer sheets 16, 17 of the front panel 7 are kept flat in FIG. 2, at least the outer sheet 17 of the inner and outer sheets 16, 17 is formed with the gathers upon contraction of the front waist elastic members 18.

The rear panel 8 in FIG. 2 comprises an inner sheet 21 facing the wearer's skin, an outer sheet 22 facing the wearer's garment and rear waist elastic members 23 sandwiched between these inner and outer sheets 21, 22. The inner and outer sheets 21, 22 are joined to each other with hot melt adhesives 64 and the rear waist elastic members 23 are attached under tension in the transverse direction X to at least one of the inner and outer sheets 21, 22 with hot melt adhesives (not shown). While the inner and outer sheets 21, 22 are kept flat in FIG. 2, at least the outer sheet 22 of the inner and outer sheets 21, 22 is formed with the gathers 70 (See FIGS. 1 and 3) defined by crests 71 and troughs 72 repeating circumferentially thereof as the front panel 7 is the case upon contraction of the rear waist elastic members 23. The rear waist elastic members 23 comprise, as will be seen in FIG. 1, a plurality of upper elastic members 23*a* closely spaced one from another and circumferentially extending along a peripheral edge 12*a* of the waist-opening 12 and a plurality of lower elastic members 23*b* spaced one from another and more widely than the upper elastic members 23*a* in the vertical direction Z.

The central panel 6 comprises a liquid-pervious inner sheet 31, a liquid-impervious outer sheet 32 and a bodily fluid-absorbent core 33 sandwiched between these inner and outer sheets 31, 32. Opposite side edges of the outer sheet 32 are folded inwardly of the diaper 1 to form a pair of leak-barriers 34 opposed to each other in the transverse direction X. Each of these leak-barriers 34 has front and rear end portions 35*a*, 35*b* attached to the inner sheet 31 and/or the outer sheet 32, an inner edge 36 extending in the front-back direction Y and adapted to come close to or in contact with the wearer's skin and an outer edge 37 corresponding to the line along which the outer sheet 32 has been folded and extending in the front-back direction Y. The leak-barrier 34 is formed along the inner edge with a sleeve 38 within which at least one elastic member 39 is attached under tension in the front-back direction Y to the inner surface of the sleeve 38 with hot melt adhesives (not shown).

The central panel 6 further includes a front end portion 42, a rear end portion 43 and an intermediate portion 41 extending between these two end portions 42, 43. The front end portion 42 overlaps the outer sheet 17 of the front panel 7 (See FIG. 1) and the rear end portion 43 overlaps the outside of the rear panel 8. The intermediate portion 41 extends in the front-back direction Y between the front panel 7 and the rear panel 8 to define the crotch region.

The front end portion 42 includes a front end 42*a* defined by at least the outer sheet 32 of the inner and outer sheets 31, 32, a pair of front side edges 42*b* being opposite in the transverse direction X and a pair of front corner regions 42*c* defined by intersection of the front end 42*a* and the front side edges 42*b* and being opposite in the transverse direction X. In the illustrated example, the front side edges 42*b* are extensions of the outer edges 37 of the leak-barriers 34, respectively. The front end portion 42 is joined to the outer sheet 17 of the front panel 7 with hot melt adhesives 62.

The rear end portion 43 includes a rear end 43*a* defined by at least the outer sheet 32 of the inner and outer sheets 31, 32, a pair of rear side edges 43*b* being opposite in the transverse direction X and a pair of rear corner regions 43*c* defined by intersection of the rear end 43*a* and the rear side edges 43*b* and being opposite in the transverse direction X. In the illustrated example, the rear side edges 43*b* are extensions of the outer edges 37 of the leak-barriers 34, respectively. The rear end portion 43 is joined to the outer sheet 22 of the rear panel 8 with hot melt adhesives 63. It should be noted that, in the rear end portion 43 of FIG. 2, the core 33 is partially shown by partially cutting away the inner sheet 31. The inner and outer sheets 31, 32 sandwiching the core 33 extend forward beyond the core 33 as viewed in FIG. 2 and are put flat and joined together with hot melt adhesives 65 outside the periphery of the core 33.

In such developed diaper 1*a*, at least one of the paired front corner regions 42*c* defined in the front end portion 42 and at least one of the paired rear corner regions 43*c* defined in the rear end portion 43 are not joined to the outside of the waist region 11 and thereby respectively define gripper regions 80 adapted to be held with the fingers. Herein, of the gripper regions 80, the gripper region defined in the front end portion 42 refers to a front gripper region 80*a* and the gripper region defined in the rear end portion 43 refers to a rear side gripper region 80*b*. A width dimension A of such gripper region 80 measured from the front side edge 42*b* or the rear side edge 43*b* in the transverse direction X as well as a dimension B thereof measured from the front end 42*a* or the rear end 43*a* in the front-back direction Y is in a range of 5 to 40 mm and to grip easily, more preferably in a range of 10 to 40 mm. If these dimensions A and B are smaller than 5 mm, the gripper region 80 would be difficult to grip, and if these dimensions A and B are larger than 40 mm, the joining of the central panel 6 and the waist region 11 would be too weak. The front end portion 2 and the rear end portion 43 except the gripper regions 80 are entirely or partially joined to the waist region 11 with hot melt adhesives 63. In the case exemplarily shown in FIG. 2, the front end portion 42 and the rear end portion 43 except the gripper regions 80*a*, 80*b* are entirely joined to the waist region 11 so that a pair of the front side corner regions 42*c* and a pair of the rear side corner regions 43*c* define the gripper regions 80*a*, 80*b*.

Figure 3:
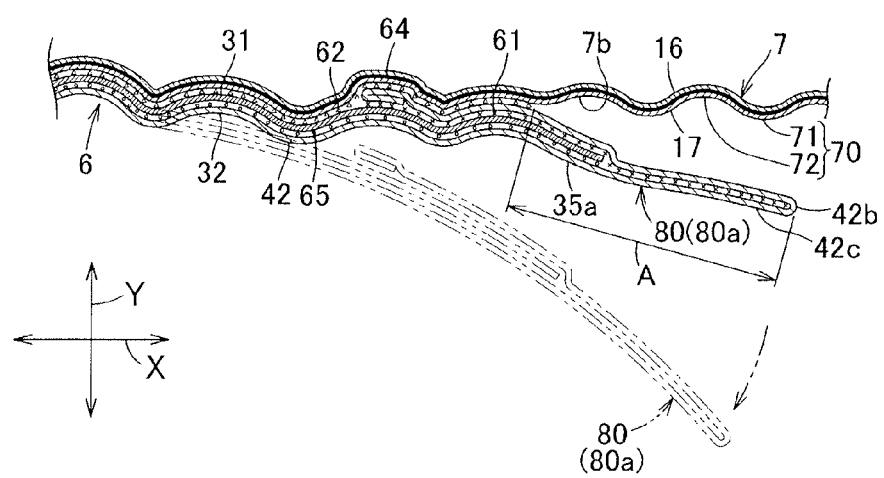
FIG. 3 is a sectional view of the diaper taken along the line in FIG. 1.

FIG. 3 shows a sectional view taken along the line in FIG. 1 which extends across one of the gripper regions 80*a* defined by the front side corner region 42*c* in the front end portion 42 of the central panel 6. This line III-III is shown in FIG. 2 also as reference. Referring to FIG. 3, the outer surface of the front panel 7 formed of the inner and outer sheets 16, 17 joined to each other with hot melt adhesives 64 is formed with the gathers 70 comprising the crests 71 and the troughs 72 repetitively alternating in the transverse direction X. While the front end portion 42 of the central panel 6 is joined to the outer sheet 17 with hot melt adhesives 62, the front side corner regions 42*c* in the front end portion 42 are not joined to the outer sheet 17 to define the front side gripper regions 80*a*. The dimension A of the front side gripper region 80*a* is the dimension measured from the front side edge 42*b* in the transverse direction X. In the front end portion 42, the inner and outer sheets 31, 32 are joined to each other with hot melt adhesives 65 and portions of the outer sheet 32 defining the leak-barriers 34 are joined to the inner sheet 31 with hot melt adhesives 61. In the diaper 1 having the preferred front side gripper regions 80a, a region 7b of the front panel 7 overlapping the front side gripper region 80a is formed with at least two of the crests 71 or the troughs 72 and a gap is formed between the front edge 42a and the front side edge 42b cooperating with each other to define the front side gripper region 80a and the front panel 7. This gap facilitates the front side gripper region 80a to be identified and to be held with the fingers. In the front side gripper region 80a, the layers of the folded outer sheet 32 overlaps each other and sandwich the inner sheet 31, resulting in sufficient thickness and stiffness and thereby facilitating the gripper region to be held by a user's or caretaker's fingers.

Figure 4:
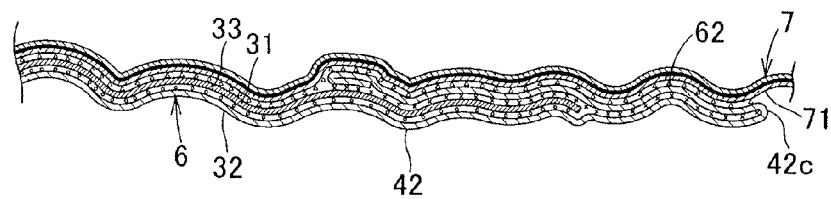
FIG. 4 is a sectional view of the diaper taken along the line IV-IV in FIG. 1.

Referring to FIG. 4, the front end portion 42 of the central panel 6 is joined along a periphery of the front side gripper region 80a to the outer sheet 17 of the front panel 7 with hot melt adhesives 62 (See FIG. 2 also). A range in which the front end portion 42 of the central panel 6 is joined to the outer sheet 17 corresponds to a coating range of hot melt adhesives 62 and this coating range exemplarily illustrated in FIG. 2 is a substantially entire area of the front end portion 42 except the front side corner regions 42c defining a pair of the front side gripper regions 80a. In the same way as in the case of the front end portion 42, a range in which the rear end portion 43 of the central panel 6 is joined to the rear panel 8 corresponds to a coating range of hot melt adhesives 63 and this coating range exemplarily illustrated in FIG. 2 is a substantially entire area of the rear end portion 43 except the rear side corner regions 43c defining a pair of the rear side gripper regions 80b.

Figure 5:
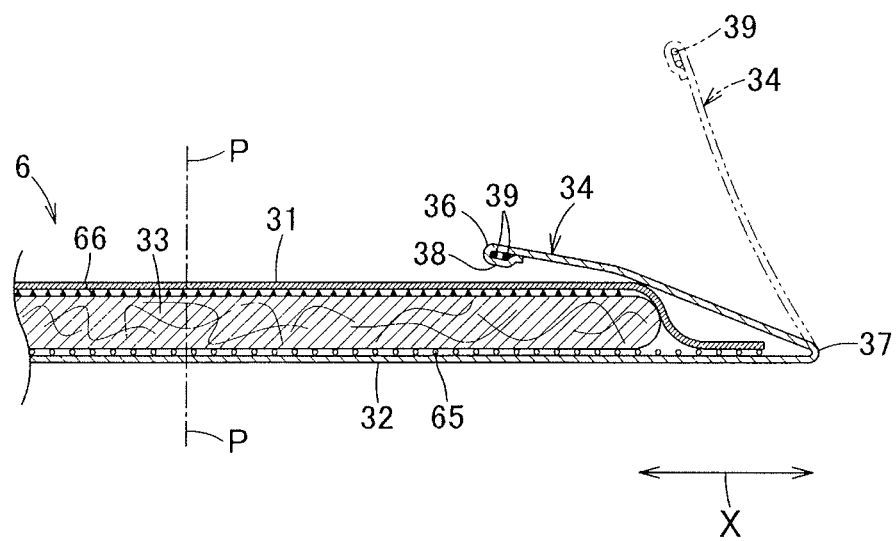
FIG. 5 is a sectional view of the diaper taken along the line V-V in FIG. 2.

Referring to FIG. 5, the inner sheet 31 constituting the central panel 6 is joined to the inner surface of the core 33 with hot melt adhesives 66. The outer sheet 32 is joined to the outer surface of the core 33 with hot melt adhesives 65 and portions of the outer sheet 32 extending outward from the peripheries of the core 33 in the transverse direction X are joined to the inner sheet 31. The portions of the outer sheet 32 extending outward from the peripheries of the inner sheet 31 in the transverse direction X are folded onto the inner sheet 31 to form the leak-barriers 34. Each of the leak-barriers 34 has the inner edge 36 and the outer edge 37 wherein the elastic member 39 is joined under tension in the front-back direction Y to the inner surface of the sleeve 38 formed of the folded inner edge 36. Imaginary lines in FIG. 5 indicate one of the leak-barriers 34 raising itself on the inner sheet 31 under contraction of the elastic member 39 when the diaper 1 is put on the wearer's body as illustrated in FIG. 1.

For the diaper 1 constructed in this manner, the front end portion 42 may be pulled apart from the front panel 7 by holding one of the front side gripper regions 80a with one hand and by holding the front panel 7 with the other hand to peel off the front end portion 42 from the front panel 7. In a similar way, the rear end portion 43 may be pulled apart from the rear panel 8 by holding one of the rear side gripper regions 80b with one hand and by holding the other rear side gripper region 80b with the other hand to peel off the rear end portion 43 from the rear panel 8.

It should be understood here that the manner in which the front end portion 42 is peeled off the front panel 7 includes one or more of the following: (i) the front end portion 42 joined to the front panel 7 with hot melt adhesives 62 is peeled off the front panel 7 at the hot melt adhesives 62, (ii) the inner and/or outer sheets 31, 32 forming the front end portion 42 is/are torn around hot melt adhesives 62, or (iii) the outer sheet 17 constituting the front panel 7 is torn around hot melt adhesives 62. In other words, the front panel 7 and/or the rear panel 8 is/are separably joined to the central panel 6 so that the front panel 7 and/or the rear panel 8 is/are peelable off the central panel 6 in one or more of the manners (i)-(iii) discussed immediately above.

To assure that the front end portion 42 can be peeled off from the front panel 7 by using the front side gripper regions 80a, the amount per unit area of hot melt adhesives 62 applied to the front end portion 42 may be appropriately adjusted or the coating pattern such as dotted pattern, spiral pattern or beaded pattern may be appropriately selected. While the coating range of hot melt adhesives 62 extends over the entire area of the front panel 7 except the front side gripper regions 80a in the example shown in FIG. 2, if the front end portion 42 includes, in addition to the front side gripper regions 80a, one or more regions requiring no coating of the adhesives, the coating area and the amount of the adhesive in the front end portion 42 can be correspondingly reduced, facilitating the front end portion 42 to be peeled off from the front panel 7.

According to the present embodiment, the rear end portion 43 of the central panel 6 may be separated from the rear panel 8 in the same manner as the front end portion 42 is used to separate from the rear panel 8. To assure that the central panel 6 can be peeled off from the rear panel 8, hot melt adhesives 63 may be used in the same manner as hot melt adhesives 62.

For the diaper 1 in which one of the front panel 7 and the rear panel 8 is not required to have the gripper regions 80, it will be no more necessary to form the outer sheet 17 or the outer sheet 22 with the gathers 70 serving to facilitate the gripper regions 80 to be held. Therefore, for such front or rear panel 7, 8, the associated elastic members 18 or 23 may be at least partially eliminated or an elastic sheet free from gathering formation may be used as the outer sheet 17 or 22.

The inner and outer sheets 16, 17 of the front panel 7 and the inner and outer sheets 21, 22 of the rear panel 8 may be formed of a nonwoven fabric of thermoplastic synthetic fibers, a plastic film, a laminated sheet consisting of such nonwoven fabrics and plastic films, or the like. The inner sheet 31 in the central panel 6 may be formed of a liquid-pervious nonwoven fabric, a perforated plastic film, or the like. The outer sheet 32 may be formed of a liquid-impervious plastic film, a laminated sheet consisting of such films and nonwoven fabrics, or the like. The core 33 may be formed of a liquid-absorbent material assembly such as fluff pulp fibers, a mixture of fluff pulp fibers and super-absorbent polymer particles or the like wrapped with a tissue paper or other liquid-pervious nonwoven fabrics.

In the case of the diaper 1 constructed so that the central panel 6 can be separated from the waist region 11, the central panel 6 and the waist region 11 may be separated from each other and may be respectively reused or discarded after the diaper 1 has been used. Particularly when the central panel 6 has been soiled with body wastes, such soiled central panel 6 may be discarded separately of the not soiled waist region 11. This is preferable from the viewpoint of recycling of resources as well as from the view point of sanitary affairs. For the diaper 1 of which the waist region 11 comprises the front panel 7 and the rear panel 8 as in the illustrated example, it is possible to construct the diaper 1 so that the front panel 7 and the rear panel 8 may be separated from each other and reused or discarded, respectively.

Figure 6:
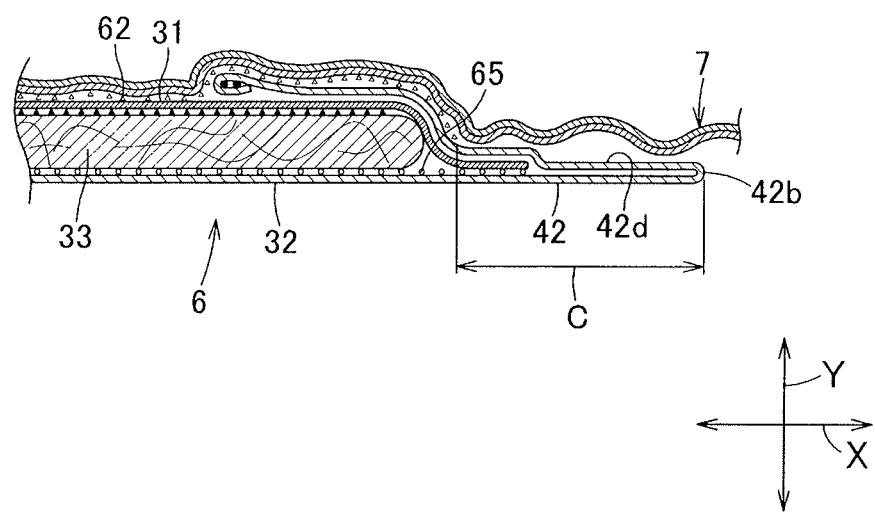
FIG. 6 is a sectional view of the diaper taken along the line VI-VI in FIG. 1, illustrating one preferred embodiment of the wearing article.

The line VI-VI extends along the lower end 7d which extends, in turn, in the transverse direction X in the front panel 7 as seen in FIG. 1 and FIG. 6 shows a sectional view taken along the line VI-VI. The lower end 7d extends in the transverse direction X across the central panel 6 to the side edges 7a of the front panel 7 (See FIG. 7 also). In the developed diaper 1a shown in FIG. 7, the front end portion 42 of the central panel 6 is associated with the front panel 7 in an alternative manner particularly in the vicinity of the lower end 7d and a region extending in parallel to this lower end 7d. Specifically, in addition to the gripper regions 80, regions 42d facing the lower end 7d and the regions extending in parallel to the lower end 7d may be left not joined to the front panel 7. These regions 42d form second gripper regions, in other words, auxiliary gripper regions adapted to complement the gripper regions 80. The regions 42d include regions in which the front side edges 42b intersect with the lower end 7d as viewed in the developed diaper 1a of FIG. 7. Each of the regions 42d preferably have a dimension C as measured from each of the front side edges 42b in the transverse direction X at least of 10 mm and a dimension D as measured from the lower end 7d in the front-back direction Y in a range of 10 to 40 mm. An upper limit of the dimension C is preferably defined by the dimension not extending beyond the inner edges 36 of the respective leak-barriers 34.

Figure 7:
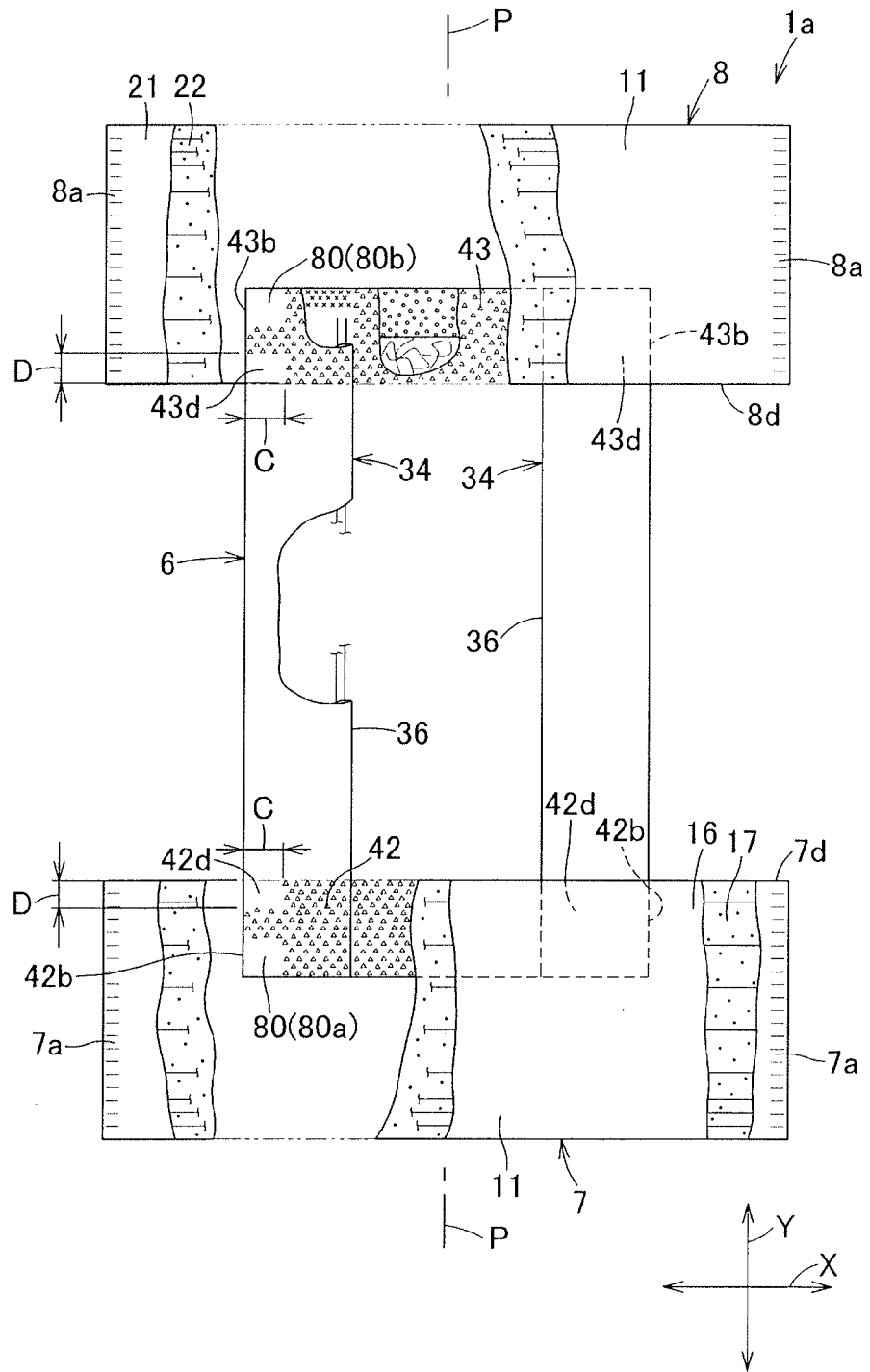
FIG. 7 is a view similar to FIG. 2, showing the pant-type diaper of FIG. 6.

In a similar manner to the front end portion 42, regions 43d in the rear end portion 43 of the central panel 6 facing the lower end 8d and the regions extending in parallel to the lower end 8d may be left not joined to the rear panel 8. These regions 43d form third gripper regions, in other words, auxiliary gripper regions adapted to complement the gripper regions 80. The lower edge 8d of the rear panel 8 extends in the transverse direction X across the central panel 6 to the side edges 8a of the rear panel 8. The regions 43d include regions in which the lower end 8d intersects with the rear side edges 43b as viewed in the developed diaper 1a of FIG. 7. Each of the regions 43d preferably a dimension C as measured from each of the rear side edges 43b in the transverse direction X at least of 10 mm. A dimension D as measured from the lower end 8d in the front-back direction Y in FIG. 7 is at least 10 mm and more preferably in a range of 10 to 40 mm. An upper limit of the dimension C is preferably defined by the dimension not extending beyond the inner edges 36 of the respective leak-barriers 34.

While how to use the regions 42d and the regions 43d is not specified, by way of example, for the used diaper 1, the gripper regions 80b of the central panel 6 may be first used to peel off the rear end portion 43 from the rear panel 8 and then the regions 42d of the central panel 6 may be used as the gripper regions to separate the central panel 6 from the front panel 7. In this case, the gripper regions 80a of the front end portion 42 are not used and therefore it is unnecessary to provide the diaper 1 with such gripper regions 80a of the front end portion 42. With the diaper 1 for baby, there is possibility that the wearer might fiddle the gripper regions 80a and, in considering this, preferably the front end portion 42 of the central panel 6 may be provided with not the gripper regions 80a but the regions 42d serving as the second gripper regions and the rear end portion 42 may be provided with the gripper regions 80b. In other words, the gripper region(s) may be provided in any one or more of the four corner regions in the central panel 6. How to combine the gripper region(s) with the second and third gripper regions is also a matter to be designed by the manufacturer. On other words, the diaper 1 may be implemented to have none of the second and third gripper regions or to have at least one of the second and third gripper regions. It should be appreciated here that the embodiment illustrated in FIGS. 1 through 5 may be at least partially applied to the diaper 1 according to the embodiment illustrated in FIGS. 6 and 7.

Figure 8:
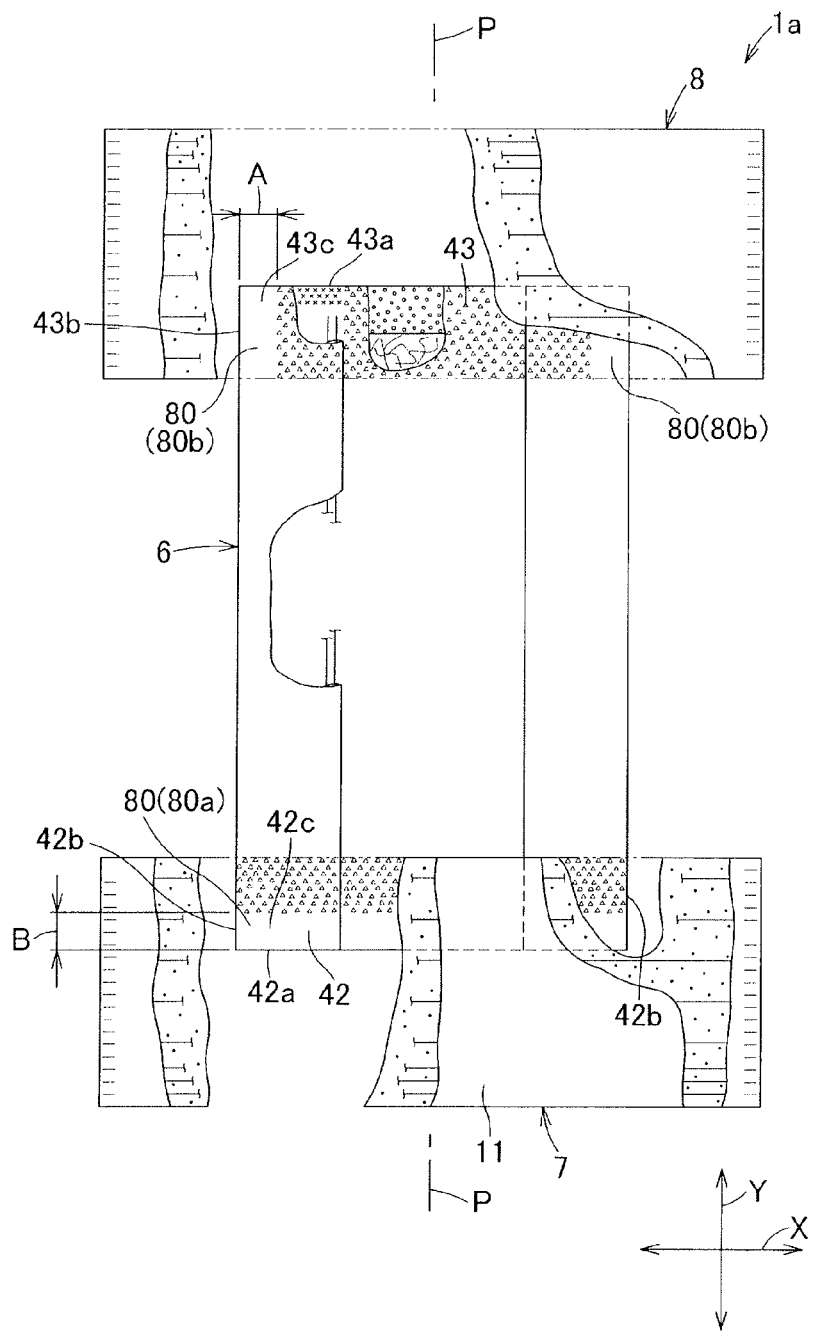
FIG. 8 is a view similar to FIG. 2, showing the pant-type diaper according to another preferred embodiment differing from the embodiment shown in FIG. 7.

In the developed diaper 1a according to another embodiment of the present invention shown in FIG. 8, the front end portion 42 of the central panel 6 is formed with a single front side gripper region 80 having a dimension B in the front-back direction Y and extending from one of the front side edge 42b to the other front side edge 42b. In the diaper 1 as well as the developed diaper 1a shown in FIGS. 1 through 7, the front side gripper regions 80a and/or the rear side gripper regions 80b formed in the corner regions of the front end portion 42 and/or the rear end portion 43 may be appropriately enlarged in the transverse direction X as exemplarily illustrated in FIG. 8 in which this occurs in the front end portion 42. Referring to FIG. 8, the rear end portion 43 of the developed diaper 1a is formed with the rear side gripper region 80b having a dimension A in the transverse direction X and extending across the rear end portion 43 in the front-back direction Y. While not illustrated, in the diaper 1 as well as the developed diaper 1a shown in FIGS. 1 through 8, the front side gripper regions 80a and/or the rear side gripper regions 80b may be appropriately enlarged in the transverse direction X and in the front-back direction Y. However, there is possibility that the baby, the wearer of the diaper 1, might unnecessarily operate the gripper regions. Considering this, the dimensions A and B are preferably set to be as small as possible.

In a pant-type wearing article such as the diaper 1, whether the leak-barriers 34 are provided or not is a matter to be designed by the manufacturer. In other words, the diaper 1 as well as the developed diaper 1a exemplarily shown in FIGS. 1 through 8 may be replaced by an embodiment according to which none of the leak-barriers 34 is provided without departing from the present invention. In the diaper 1 provided with none of the leak-barriers 34, the regions corresponding to the outer edges 37 (See FIG. 2) define the side edges of the intermediate portion 41 of the central panel 6. While the central panel 6, the front panel 7 and the rear panel 8 in the developed diaper 1a of FIG. 2 are exemplarily illustrated to have rectangular shapes, respectively, the shapes of these panels 6, 7, 8 may be replaced by appropriate shapes. The central panel 6 exemplarily illustrated to contain the core 33 may be replaced by the central panel 6 containing no core 33. All of hot melt adhesives can be replaced by the other types of joining means, such as thermal bonds and sonic bonds.

The first aspects of the present invention described above may be arranged in at least the following items:

A pant-type wearing article having a vertical direction and a transverse direction, comprising a front panel, a rear panel and a central panel, side edges of the front panel opposed in the transverse direction being joined to side edges of the rear panel opposed in the transverse direction to form an annular waist region, the central panel being folded in the vertical direction to define two upper end portions, and one of the two upper end portions is joined to an outside of the front panel and other of the two upper end portions is joined to an outside of the rear panel, wherein: at least one of the front panel and the rear panel is provided with a plurality of elastic members extending in the transverse direction under tension and adapted to be formed with gathers forming crests and troughs repeating in the transverse direction upon contraction of the elastic members; the central panel has the one of the two upper end portions separably joined to the front panel and the other of the two upper end portions separably joined to the rear panel; and the two upper end portions respectively have ends extending in the transverse direction and side edges extending in the vertical direction wherein the side edges intersect with the ends to form a pair of corner regions in each of the ends and at least one of the corner regions overlaps the gathers and not joined to the outer surface of the waist region to define a gripper region adapted to be held by fingers.

One or more aspect of the present invention described in the above item (i) may provide one or more of the following advantageous effects:

At the respective end portions, the side edges intersect with the end to form a pair of the corner regions of which at least one defines a gripper region adapted to be easily held by the fingers. Holding this gripper region by one hand and holding the waist region formed of the front panel and the rear panel by the other hand, the gripper region and the waist region may be pulled apart from each other to peel off the ends of the central panel from the waist region.

Additionally, one or more of the following embodiments are provided in accordance with further aspects:

(ii) The gripper region has a dimension measured from one of the ends forming the corner region in the vertical direction as well as a dimension measured from one of the side edges forming the corner region in the transverse direction in a range of 5 to 40 mm.

(iii) The outside of the waist region defined by the front panel and the rear panel is formed with the gathers upon contraction of the elastic members.

(iv) A region on the outside of the waist region overlapping a range defined by a dimension of 5 mm measured from the one of the side edges in the gripper region in the transverse direction is formed with at least two of the crests or the troughs.

(v) At least one of the front panel and the rear panel has an end extending between the side edges to intersect with the central panel in the transverse direction and to be joined to the central panel and wherein the central panel includes a point at which one of the side edges intersects with the end and, in the vicinity of the point, an auxiliary gripper region having a dimension as measured from the side edge in the transverse direction as well as a dimension as measured from the end in the vertical direction of at least 10 mm and not joined to the waist region.

(vi) The central panel comprises an inner sheet and an outer sheet, the inner sheet being formed on the inner side thereof with a pair of leak-barriers extending along the side edges to the end portions and, in the corner regions, the leak-barriers, the inner sheet and the outer sheet overlap one another and are joined together to form at least a part of the gripper regions.

(vii) The gripper region extend in parallel to at least one of the ends and the side edges beyond the range.

According to the embodiments in the above (ii) to (vii), the advantageous effect(s) set forth above is/are better ensured. Further advantageous effects of the respective embodiments may be obtained as discussed in the respective related descriptions.

The invention claimed is:

1. A pants-type wearing article having a vertical direction and a transverse direction, said wearing article comprising:
    a front panel, a rear panel and a central panel,
    wherein
    said front panel includes side edges opposed in said transverse direction,
    said rear panel includes side edges opposed in said transverse direction and joined to the side edges of the front panel to form an annular waist region,
    said central panel is folded in said vertical direction to define two upper end portions,
    one of said two upper end portions is joined to an outer surface of said front panel and the other of said two upper end portions is joined to an outer surface of said rear panel,
    at least one of said front panel and said rear panel is provided with a plurality of elastic members extending in said transverse direction under tension and formed with gathers forming crests and troughs repeating in said transverse direction upon contraction of said elastic members,
    said central panel has said one of said two upper end portions separably joined to said front panel to define a bonding region elongated in the transverse direction, and the other of said two upper end portions separably joined to said rear panel to define a further bonding region elongated in the transverse direction, and
    said two upper end portions respectively have
        ends extending in said transverse direction; and
        side edges extending in said vertical direction and intersecting with said ends to form a pair of corner regions in each of said upper end portions,
    at least one of said corner regions overlaps said gathers and is free of direct joining to an outer surface of said waist region to define a gripper region adapted to be held by a user's or caretaker's fingers, and
    an entirety of the upper end portions excluding the pair of corner regions are joined to the front and rear panels correspondingly.

2. The wearing article defined by claim 1, wherein said gripper region has a dimension measured from one of said ends forming said corner region in said vertical direction as well as a dimension measured from one of said side edges forming said corner region in said transverse direction in a range of 5 to 40 mm.

3. The wearing article defined by claim 2, wherein
    said gripper region extends in parallel to at least one of said ends forming said corner region and said side edges forming said corner region, and
    said gripper region has a dimension measured from one of said ends forming said corner region in said vertical direction as well as a dimension measured from one of said side edges forming said corner region in said transverse direction in a range of 10 to 40 mm.

4. The wearing article defined by claim 1, wherein the outer surface of said waist region defined by said front panel and said rear panel is formed with said gathers upon contraction of said elastic members.

5. The wearing article defined by claim 1, wherein a region on the outer surface of said waist region overlapping a range defined by a dimension of 5 mm measured from said one of said side edges in said gripper region in said transverse direction is formed with at least two of said crests or at least two of said troughs.

6. The wearing article defined by claim 1, wherein
    said central panel comprises an inner sheet and an outer sheet,
    said inner sheet is formed on an inner side thereof with a pair of leak-barriers extending along said side edges to said two upper end portions, and
    in said at least one of said corner regions, a corresponding one of said leak-barriers, said inner sheet and said outer sheet overlap one another and are joined together to form at least a part of said gripper region.

7. The wearing article defined by claim 1, wherein the bonding region and the further bonding region extend to the side edges of the corresponding front and rear panels in the transverse direction.

8. The wearing article defined by claim 7, further comprising a pair of leak-barriers opposing each other in the transverse direction, wherein a width of one of the corner regions is less than a width of one of the leak-barriers in the transverse direction.

9. The wearing article defined by claim 8, wherein
at least one of said front panel and said rear panel has an end extending between said side edges of the at least one of said front panel and said real panel, intersecting with said central panel in said transverse direction and directly joined to said central panel,
each of the corner regions of the upper end portion separably joined to the at least one of said front panel and rear panel includes first and second corner areas opposing each other in the vertical direction and separated from each other by the bonding region or the further bonding region.

10. The wearing article defined by claim 9, wherein
the first corner area is defined by (a) one of the side edges forming the corner regions and (b) the end of the upper end portion, and
the second corner area is defined by (a) said one of the side edges forming the corner regions and (b) the end of the at least one of said front panel and rear panel.

11. The wearing article defined by claim 1, wherein
at least one of said front panel and said rear panel has an end extending between said side edges of the at least one of said front panel and said real panel, intersecting with said central panel in said transverse direction and directly joined to said central panel.

12. The wearing article defined by claim 11, wherein
the gripper region continuously extends in the vertical direction between (a) the end of the upper end portion separably joined to the at least one of said front panel and rear panel and (b) the end of the at least one of said front panel and rear panel.

13. The wearing article defined by claim 12, further comprising a pair of leak-barriers opposing each other in the transverse direction, wherein a width of one of the corner regions is less than a width of one of the leak-barriers in the transverse direction.

* * * * *